(12) United States Patent
Satou et al.

(10) Patent No.: US 6,523,567 B2
(45) Date of Patent: Feb. 25, 2003

(54) APPARATUS AND PROCESS FOR SUPPLYING GAS

(75) Inventors: Tetsuya Satou, Tokyo (JP); Tsutomu Kikuchi, Tokyo (JP); Akira Nishina, Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 10/131,666

(22) Filed: Apr. 24, 2002

(65) Prior Publication Data

US 2002/0117222 A1 Aug. 29, 2002

Related U.S. Application Data

(62) Division of application No. 09/605,782, filed on Jun. 28, 2000.

(30) Foreign Application Priority Data

Jul. 1, 1999 (JP) .............................................. 11-187953

(51) Int. Cl.[7] ................................................. F17D 1/00
(52) U.S. Cl. ...................................... 137/597; 137/240
(58) Field of Search .................................. 137/597, 240

(56) References Cited

U.S. PATENT DOCUMENTS

| | | |
|---|---|---|
| 5,205,322 A | 4/1993 | Merick et al. |
| 5,305,630 A | 4/1994 | Molozay et al. |
| 5,313,982 A | 5/1994 | Ohmi et al. |
| 5,488,967 A | 2/1996 | Minami et al. |
| 5,900,214 A | 5/1999 | Girard et al. |

Primary Examiner—John Fox
(74) Attorney, Agent, or Firm—Merchant & Gould P.C.

(57) ABSTRACT

There is provided a gas supplying apparatus capable of rapidly switching the gas to be supplied to an instrument and preventing reactive gases from mixing each other. The gas supplying apparatus comprises: a 4-way block valve which is a main switching valve 10, having two inflow ports 11, 12 and two outflow ports 13, 14; an instrument connection passage 1 connected to an instrument, such as an analyzer, to which the outflow ports 13 is connected; an exhaust passage 4 to which the two outflow ports 14 is connected; common gas supplying passages 2, 3 respectively connected to the two inflow ports 11, 12 of the 4-way block valve; a switching valve(s) 20 made of a 2-connected 3-way block valve(s) or a 4-way block valve(s) connected to the at least one of the two common gas supplying passages 2, 3; and two gas supplying passages 21, 22 switchably connected the 2-connected 3-way block valve(s) or the 4-way block valve(s).

1 Claim, 5 Drawing Sheets

APPARATUS AND PROCESS FOR SUPPLYING GAS

This application is a division of U.S. Application Ser. No. 09/605,782 filed Jun. 28, 2000.

BACKGROUND OF INVENTION

1. Field of the Invention

The present invention relates to an apparatus and a process for supplying gas, more specifically to an apparatus and a process for selecting any one of a plurality of gases and then supplying them to an instrument, in particular a trace impurity analyzer such as an atmospheric-pressure ionization mass spectrometer (APIMS).

2. Description of Prior Art

Recently, in the field of gas analysis, it is increasingly important to consecutively and rapidly analyze a plurality of sample gases, using a same analyzer. For this purpose, a gas passage switching means such as in the Japanese laid-open publication Hei No. 10-122498, has been used for switching a sample gas to be supplied to a gas analyzer.

However, in the case of switching sample gas by opening and closing a plurality of valves, the gas could stagnate inside the valves or inside the pipings of the vicinity of the valves, and in the case of switching the kind of gas, a different kind of gas could be mixed with the sample gas. As a different kind of gas mixed with the sample gas becomes an impurity component with respect to the sample gas, in particular in the case of analyzing trace impurities present in high-purity gas using a high-sensitivity gas analyzer such as an atmospheric-pressure ionization mass spectrometer (APIMS) or the like, different kinds of gases mixed therein could greatly affect the analysis results, with only a small quantity. Furthermore, if the sample gas reacts to the gas mixed therein, as in the case of hydrogen and oxygen, there is an undesirable possibility that both gases react each other and explode.

For this reason, in the previous gas analyzer, a purge gas is subject to flow in order to completely remove the sample gas of the previous step whenever sample gas is analyzed. However, the above operation requires a long time, and thus a plurality of sample gases could not be analyzed in a short time. In addition, in the case of using a plurality of valves, if two or more valves become in the opening state simultaneously, owing to some trouble in the valves, not only the analysis experiences trouble, but also the gases could undesirably react to one another. Moreover, in such cases, as the operation of the analyzer should be stopped for exchanging the broken-down valves, it took a very long time to reinitiate the operation.

SUMMARY OF THE INVENTION

The present invention aims to provide with an apparatus and a process for supplying gas capable of rapidly switching the gas to be supplied to an instrument and preventing reactive gases from mixing one another.

To achieve the object, a gas supplying apparatus according to the present invention comprises: a 4-way block valve which is a main switching valve, having two inflow ports and two outflow ports; an instrument connection passage connected to an instrument, such as an analyzer, to which the one of the two outflow ports is connected; an exhaust passage to which the other of the two outflow ports is connected; common gas supplying passages respectively connected to the two inflow ports of the 4-way block valve; a switching valve(s) made of a 2-connected 3-way block valve(s) or a 4-way block valve(s) connected to the at least one of the two common gas supplying passages; and two gas supplying passages switchably connected to the 2-connected 3-way block valve(s) or the 4-way block valve(s).

Furthermore, the 2-connected 3-way block valve(s) of the switching valve(s) comprises: an outflow port connected to the common gas supplying passage; and first and second inflow ports connected to the two gas supplying passages respectively; and the 4-way block valve(s) of the switching valve(s) comprises: first and second outflow ports wherein the first outflow port is connected to the common gas supplying passage and the second outflow port is connected to the exhaust passage; and first and second inflow ports connected to the two gas supplying passages respectively.

Furthermore, the 2-connected 3-way block valve(s) of the switching valve(s) comprises: first and second inflow ports; an outflow port; first valve for switching the first inflow port and the outflow port between a communicating state and a blocking state and second valve for switching the second inflow port and the outflow port between the communicating state and the blocking state; wherein the first and the second valves are operated in such a way that when the one of the first and the second valves is brought into the communicating state, the other of the first and the second valves is brought into the blocking state. An exhaust passage with a flow rate regulator is branch-connected in a flow passage communicating with the first inflow port.

On the other hand, the 4-way block valve(s) of the switching valve(s) comprises: first and second inflow ports; first and second outflow ports; first valve for switching the first inflow port and the first outflow port between a communicating state and a blocking state; second valve for switching the second inflow port and the first outflow port between the communicating state and the blocking state; third valve for switching the first inflow port and the second outflow port between the communicating state and the blocking state; fourth valve for switching the second inflow port and the second outflow port between the communicating state and the blocking state; and an exhaust passage with a flow rate regulator connected to the second outflow port wherein the valves are operated in such a way that when the first valve and the fourth valve are brought into a communicating state, the second valve and the third valve are brought into a blocking state and when the first valve and the fourth valve are brought into the blocking state, the second valve and the third valve are brought into the communicating state.

Furthermore, a process of the present invention for supplying gas by using the above-mentioned gas supplying apparatus, comprises the steps of: providing each of the two common gas supplying passages with the first and the second switching valves respectively, in the case that two kinds of gases which react to each other when mixed, are present in a plurality of gases to be supplied to the respective gas supplying passages; connecting a passage for supplying first reactive gas and a passage for supplying first non-reactive gas to the first switching valves and connecting a passage for supplying second reactive gas and a passage for supplying second non-reactive gas to the second switching valve; supplying the second non-reactive gas from the second switching valve to the main switching valve, in the case of supplying the first reactive gas to the instrument from the first switching valve via the main switching valve; switching the first switching valve supplying the first reactive gas in order to supply the first non-reactive gas, in the case of switching the gas to be supplied to the instrument to the gas coming from the first switching valve; and switching the main switching valve such that the gas to be supplied to the instrument is switched to the gas coming from the first switching valve after the concentration of the first reactive gas present in the gas to be supplied to the apparatus is lowered below a predetermined concentration.

BRIEF DESCRIPTION OF THE DRAWINGS

For fuller understanding of the nature and objects of the invention, reference should be made to the following detailed description taken in conjunction with the accompanying drawings in which.

DESCRIPTION OF PREFERRED EMBODIMENT

Figure 1:
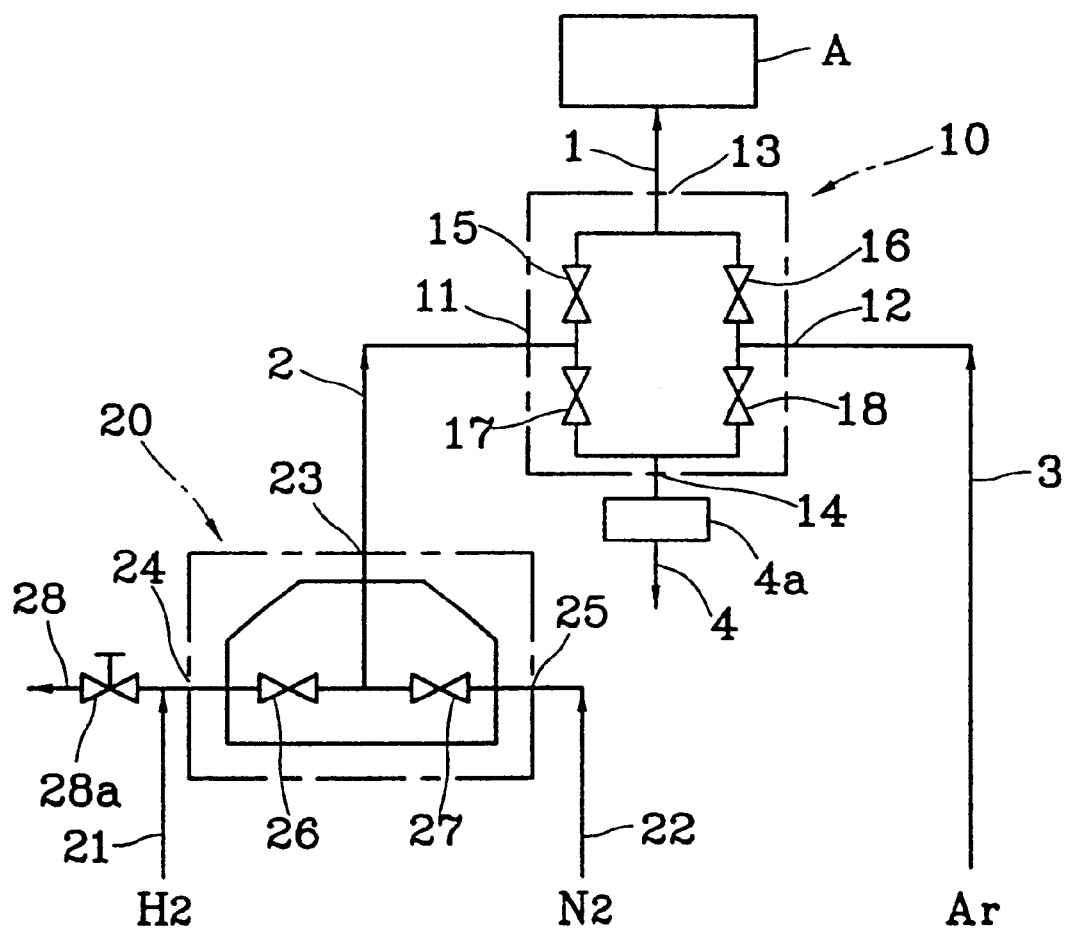
FIG. 1 is a schematic view of the first embodiment of the gas supplying apparatus according to the present invention.

FIG. 1 is a schematic view of the first embodiment of a gas supplying apparatus according to the present invention. The gas supplying apparatus is formed such that three kinds of gases are switchably supplied to the instrument such as an analyzer or the like, and comprises a main switching valve 10 connected to an analyzer A via an instrument connection passage 1, and a switching valve 20 made of 2-connected 3-way block valve, connected to the main switching valve 10 via a first common gas supplying passage 2.

The 4-way block valve as the main switching valve 10 includes first inflow port 11, second inflow port 12, first outflow port 13, second outflow port 14, first valve 15, second valve 16, third valve 17 and fourth valve 18, wherein the first inflow port 11 and the second inflow port 12 are connected to the first common gas supplying passage 2 and the second common gas supplying passage 3 respectively, and the instrument connection passage 1 and an exhaust passage (or purge line) 4 with a flow rate regulator 4a are connected to the first outflow port 13 and the second outflow port 14 respectively. In this embodiment, as a switching valve is not provided in the second common gas supplying passage 3, only one kind of gas flows.

The first valve 15 brings the first inflow port 11 and the first outflow port 13 into a communicating state or a blocking state, and the second valve 16 brings the second inflow port 12 and the first outflow port 13 into a communicating state or a blocking state, and the third valve 17 brings the first inflow port 11 and the second outflow port 14 to a communicating state or a blocking state, and the fourth valve 18 brings the second inflow port 12 and the second outflow port 14 to a communicating state or a blocking state. The first valve 15 and the fourth valve 18 are diagonally positioned and form a group and the second valve 16 and the third valve 17 are diagonally positioned and form a group respectively. When the first valve 15 and the fourth valve 18 are brought into the communicating state, the second valve 16 and the third valve 17 are brought into the blocking state, and when one of the two groups is in the communicating state, the other group is brought into the blocking state.

Therefore, the gases supplied from the first common gas supplying passage 2 and the second common gas supplying passage 3 respectively, are supplied to the analyzer A from the first outflow port 13 via the instrument connection passage 1, or are exhausted to the exhaust passage 4 from the second outflow port 14 via the flow rate regulator 4a, by the operation of the respective valves. In other words, the gas constantly flows in the main switching valve 10, without being cut off.

The 2-connected 3-way block valve which is used as the switching valve 20 and in which two passages of gas supplying passages 21, 22 are switchably connected, includes an outflow port 23 connected to the first common gas supplying passage 2, a first inflow port 24 to which the first gas supplying passage 21 is connected, a second inflow port 25 to which the second gas supplying passage 22 is connected, a first valve 26 which brings the outflow port 23 and the first inflow port 24 into a communicating state or a blocking state, and a second valve 27 which brings the outflow port 23 and the second inflow port 25 into a communicating state or a blocking state. The first valve 26 and the second valve 27 operate such that when one of them is brought into the communicating state, the other is brought into the blocking state, and any one of the gas of the first gas supplying passage 21 or the second gas supplying passage 22 passes through the switching valve 20 and flows into the first common gas supplying passage 2. In addition, an exhaust passage 28 with a flow rate regulator 28a is branch-connected to the first gas supplying passage 21 connected to the first inflow port 24.

The flow rate regulators 4a, 28a have only to be able to regulate the gas amount flowing into the exhaust passages 4, 28 to the predetermined flow rate, and can be properly used by being selected, for example, from a flow rate variable type such as mass flow controller or needle valve, or a fixed type such as an orifice in response to the need. In addition, the exhaust passage 28 can branch off from the flow passage of the 2-connected 3-way block valve. Moreover, the second inflow port 25 can be also provided with an exhaust passage having a flow rate regulator and the exhaust passage 28 can be omitted according to the condition.

In addition, though various types are available as the 4-way block valve or the 2-connected 3-way block valve for switching the gas flow passage, a high integrated one is preferred for minimizing the gas stagnation volume in the valve body. Moreover, electropolishing treatment or chrome rich passivation treatment can be performed according to the need.

Gases to be switchably supplied can be optionally selected and not only high-purity gases such as oxygen, nitrogen, hydrogen, argon, helium, xenon, krypton, nitrogen oxide, carbon monoxide, carbon dioxide, various kinds of hydrocarbon, sulfur oxide or the like, but also gases for semiconductor materials such as silane, arsine, phosphine or the like, are possibly used. And then, as an instrument to which the gas is supplied, not only the analyzer A such as the aforementioned atmospheric pressure ionization mass spectrometer (APIMS), gas chromatograph-atmospheric pressure ionization mass spectrometer (GC-APIMS), etc., but also a semiconductor manufacturing apparatus or a gas manufacturing apparatus is possibly used.

The gas supplying apparatus formed as the above is able to switchably supply three kinds of sample gases to the analyzer A. For example, in the case that the sample gases are hydrogen, nitrogen and argon, the first gas supplying passage 21, the second gas supplying passage 22 and the second common gas supplying passage 3 are set to be supplied by hydrogen, nitrogen and argon respectively, at a proper pressure, for example, at 0.3 MPaG, and by operating 4-way block valve of the main switching valve 10 and 2-connected 3-way block valve of the switching valve 20 in a predetermined order, the gases are supplied to the analyzer A in a predetermined order, for example, in the order of nitrogen→hydrogen→argon and the impurity of the respective gases can be measured in the analyzer A.

In the case of analyzing nitrogen in the beginning, the first valve 26 and the second valve 27 in the switching valve 20 are brought into the blocking state and the communicating state respectively, while the first valve 15 and the fourth valve 18 are brought into the communicating state and the second valve 16 and the third valve 17 are brought into the blocking state, in the main switching valve 10.

Therefore, nitrogen supplied from the second gas supplying passage 22 passes through the first common gas supplying passage 2 from the inflow port 25, the second valve 27 and the outflow port 23 of the switching valve 20, and flows into the instrument connection passage 1 through the first inflow port 11, the first valve 15 and the first outflow port 13 of the main switching valve 10, thereby being supplied to the analyzer A in which the impurities are analyzed. In this case, hydrogen supplied from the first gas supplying passage 21, is exhausted from the exhaust passage 28 through the flow rate regulator 28a and argon supplied from the second common gas supplying passage 3 is exhausted from the exhaust passage 4 through the fourth valve 18 of the main switching valve 10 and the flow rate regulator 4a.

Gas switching from nitrogen to hydrogen can be performed by reversing the opening and closing state of the 2-connected 3-way block valve of the switching valve 20, and by bringing the first valve 26 into the communicating state and the second valve 27 into the blocking state. In this case, the nitrogen supplied from the second gas supplying passage 22 is temporarily brought into the flow stagnation state, since the flow passage is blocked in the second valve 27.

Gas switching from hydrogen to argon can be performed by reversing the opening and closing state of the main switching valve 10, and by bringing the first valve 15 and the fourth valve 18 into the blocking state and the second valve 16 and the third valve 17 into the communicating state. Furthermore, in this case, by reversing the opening and closing state of the 2-connected 3-way block valve of the switching valve 20, such that the first valve 26 is brought into the blocking state and the second valve 27 is brought into the communicating state, and by making nitrogen of the second gas supplying passage 22 flow into the exhaust passage 4 of the main switching valve 10 from the switching valve 20 through the first common gas supplying passage 2, the flow passages of the valve body or the inside of the pipings can be purged by nitrogen, and thus the gas switching from argon to nitrogen can be rapidly performed. In addition, the flow-stagnation time of nitrogen can be shortened as well.

Gas switching from argon to nitrogen can be obtained by reversing the opening and closing state of the main switching valve 10 such that the first valve 15 and the fourth valve 18 are brought into the communicating state and the second valve 16 and the third valve 17 are brought into the blocking state. In this analysis of nitrogen, there is enough time that the nitrogen stagnating in the second gas supplying passage 22 can be purged from the exhaust passage 4 while argon is analyzed, and thus the exact concentration of the impurities can be measured in a short time.

In addition, if the 2-connected 3-way block valve of the switching valve 20 malfunctions such that both the valves 26, 27 are brought into the communicating state together, since the mixed gas of hydrogen and nitrogen are supplied into the analyzer A, the respective impurity concentrations increase very much and thus the break-down of the switching valve 20 can be recognized from the measured valve of the analyzer A. Similarly, if the main switching valve 10 malfunctions and all the valves are brought into the communicating state, the mixed gas of argon and hydrogen, or argon and nitrogen, are supplied into the analyzer A, and thus the measuring condition greatly changes and the breakdown of the main switching valve 10 can be recognized from the measured value of analyzer A.

Figure 2:
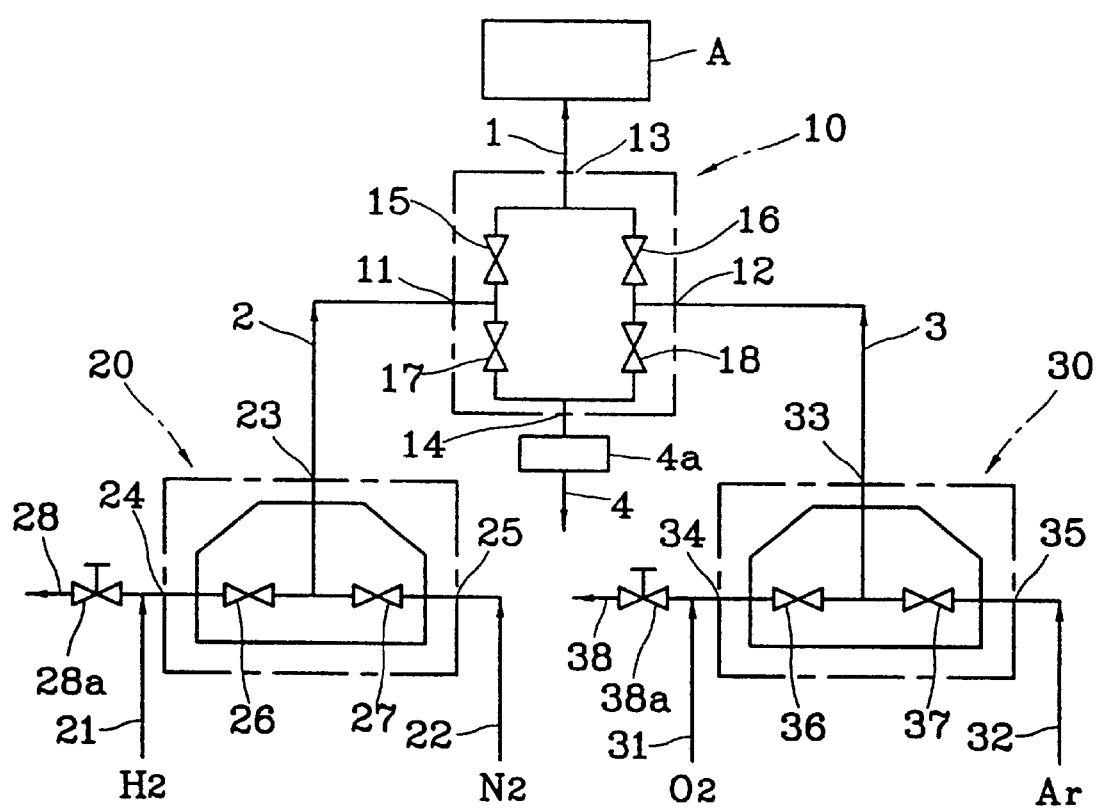
FIG. 2 is a schematic view of the second embodiment of the gas supplying apparatus according to the present invention.

FIG. 2 is a schematic view of the second embodiment of a gas supplying apparatus according to the present invention. In the gas supplying apparatus, the second common gas supplying passage 3 of the above gas supplying apparatus of the first embodiment is also provided with a switching valve 30. In the following description, the elements identical with those of the first embodiment are referred to by the same reference numerals without detailed explanation.

The 2-connected 3-way block valve as the second switching valve 30, to which two passages of gas supplying passages 31,32 are switchably connected in a similar way with the above switching valve 20, is provided with an outflow port 33 connected to the second common gas supplying passage 3, a first inflow port 34 to which the third gas supplying passage 31 is connected, a second inflow port 35 to which the fourth gas supplying passage 32 is connected, a first valve 36 for bringing the outflow port 33 and the first inflow port 34 into the communicating state or the blocking state, and a second valve 37 for bringing the outflow port 33 and the second inflow port 35 into the communicating state or the blocking state, and an exhaust passage 38 with a flow rate regulator 38a is branch-connected to the third gas supplying passage 31 connected to the first inflow port 34.

The gas supplying apparatus formed as above, not only can switchably supply four kinds of sample gases to the analyzer A, but also can safely perform switchable-supply of reactive gases. In case of containing hydrogen and oxygen as reactive gases, for example, in the case that four kinds of gases of hydrogen, oxygen, nitrogen and argon are switchably supplied, the reactive gases of hydrogen and oxygen are displaced in separate switching valves, for example, in such a way that hydrogen is connected to the first gas supplying passage 21 connected to the first switching valve 20 and oxygen is connected to the third gas supplying passage 31 connected to the second switching valve 30 respectively, while the non-reactive gases of nitrogen and argon are connected to the second gas supplying passage 22 of the switching valve 20 and the fourth gas supplying passage 32 of the switching valve 30 respectively. Moreover, it is preferable to supply the gases to the analyzer A, for example, in the order of nitrogen→hydrogen→argon→oxygen, such that hydrogen and oxygen are not to be in sequence.

In the case of analyzing nitrogen in the beginning, the first valve 26 and the second valve 27 of the first switching valve 20 are brought into the blocking state and the communicating state respectively, and the first valve 36 and second valve 37 of the second switching valve 30 are brought into the blocking state and the communicating respectively while in 4-way block valve of the main switching valve 10, the first valve 15 and the fourth valve 18 are brought into the communicating state and the second valve 16 and the third valve 17 are brought into the blocking state. Therefore, while nitrogen is supplied to analyzer A, hydrogen, oxygen and argon are continuously exhausted from the exhaust passage 28, the exhaust passage 38 and the exhaust passage 4 respectively and sequentially without stagnation, and nitrogen and argon flow in the main switching valve 10.

Gas switching from nitrogen to hydrogen can be performed by bringing the first valve 26 of the switching valve 20 into the communicating state and the second valve 27 into the blocking state. In this case, the main switching valve 10 is brought into a state in which hydrogen and argon flow therein.

Gas switching from hydrogen to argon is performed by switching, at first, by switching the supply gas to nitrogen by bringing the first valve 26 of the switching valve 20 into the blocking state and bringing the second valve 27 of the switching valve 20 into the communicating state, and then by purging the hydrogen in the passage through the first common gas supplying passage 2, the main switching valve 10 and the instrument connection passage 1 to analyzer A, with nitrogen. Therefore, after the hydrogen concentration of the passage becomes sufficiently low, the first valve 15 and the fourth valve 18 of the main switching valve 10 are brought into the blocking state, the second valve 16 and the third valve 17 of the main switching valve 10 are brought into the communicating state, and thus argon from the switching valve 30 is supplied into the analyzer A.

As above, by making the main switching valve 10 to be switched after hydrogen is sufficiently purged, even in the state that the oxygen flows into the second common gas supplying passage 3 due to the malfunction of the second switching valve 30, there is no possibility that hydrogen and oxygen are mixed in the instrument connection passage 1.

Gas switching from argon to oxygen is performed by bringing the first valve 36 of the switching valve 30 into the communicating state and the second valve 37 of the switching valve 30 into the blocking state. In this case, since nitrogen is supplied from the first switching valve 20 to the main switching valve 10, the main switching valve 10 is brought into a state in which oxygen and nitrogen flow therein, and thus hydrogen and oxygen do not mix each other.

Gas switching from oxygen to nitrogen is performed, by switching the main switching valve 10 to the nitrogen supply state, after the first valve 36 of the switching valve 30 is brought into the blocking state and the second valve 37 thereof is brought into the communicating state, and the oxygen is sufficiently purged by making argon flowing into the passage to the analyzer A. In this case, even if hydrogen flows into the main switching valve 10 due to the malfunction of the first switching valve 20, since the main switching valve 10 is switched after oxygen is sufficiently purged, there is no possibility that hydrogen and oxygen mix each other in the instrument connection passage 1. In addition, the recognition of the purge of hydrogen or oxygen can be carried out by the measured value of the analyzer A or by using another measuring means, as well as by checking the time.

As for the gas supplying apparatus formed as above described, even if the main switching valve 10 malfunctions, when hydrogen or oxygen are supplied from one of the switching valves 20, 30, argon or nitrogen is supplied from the other valves, and thus hydrogen and oxygen do not happen to flow into the main switching valve 10 at the same time and the reactive gases do not mix each other.

Moreover, even in the case that the entire valves are brought into the communicating state due to the malfunction of the main switching valve 10 during analyzing a gas, since about 50% of mixed gas is supplied to the analyzer A, the analyzing condition varies in a large scale, abnormality is generated in the measured data of impurities, and thus the malfunctioning of the main switching valve 10 can be easily recognized. In addition, even if the 2-connected 3-way block valve(switching valve 20, 30) in which the gas being analyzed flows malfunctions, since the mixed gas of hydrogen and nitrogen, or oxygen and argon are supplied to the analyzer A in the above-mentioned example, the generation of the abnormality can be easily recognized in this case as well. Furthermore, when the 2-connected 3-way block valve, in which the gas not being analyzed flows, malfunctions, for example, when the impurities are measured by supplying hydrogen from the switching valve 20, even if the switching valve 30 malfunctions so that oxygen and argon flow therein, the 4-way block valve 10 is switched after analyzing hydrogen is finished and purging is sufficiently preformed with nitrogen as above. Therefore, in the case of switching the main switching valve 10, there is no danger that oxygen and hydrogen mix in a high concentration, react to each other, and explode. In addition, since the mixed gas of oxygen and argon is supplied into the analyzer A, the generation of the abnormality of the switching valve 30 can be easily recognized, similarly as in the above case.

In addition, even in the case that one of the switching valves is exchanged due to its break-down, by controlling the main switching valve 10 such that the gas is supplied to the analyzer A from the other normal switching valve, it is possible to exchange and repair the switching valve during proceeding the operation of the analyzer A, and since purging from the switching valve after the exchanging and repairing work is performed in the same state, the analyzing operation can be restarted in a short time.

Opening and closing operation of these valves can be automatically carried out by connecting actuator for opening and closing the respective valves to an appropriate controlling means, and by controlling the actuator in a predetermined sequence. In addition, in the case that abnormal data are detected in the analyzer A, if the emergent shutting sequence for shutting all the valves of the gas passages is inputted into the control means, it can be more surely avoided that reactive gases such as oxygen and hydrogen are mixed, and the reactive gases can be safely analyzed as well.

Furthermore, non-reactive gas such as nitrogen or argon, stagnates in the gas supplying passage, since the flow passage is temporarily blocked in the switching valve at the time of analyzing the reactive gases. However, since by reversing the state of the switching valve to the communicating state at the time that the analysis of the reactive gases ends, purging can be sufficiently performed until the step of analyzing these gases comes, there is no difficulty in analyzing from ppt level to ppb level of impurities.

In the case that only two kinds of reactive gases, such as, hydrogen and oxygen, are subject to be analyzed, by using the gas supplying apparatus shown in this embodiment and organizing non-reactive gases such as nitrogen or the like, as purge gas, the analysis can be performed without the possibility that reactive gases are mixed.

Figure 3:
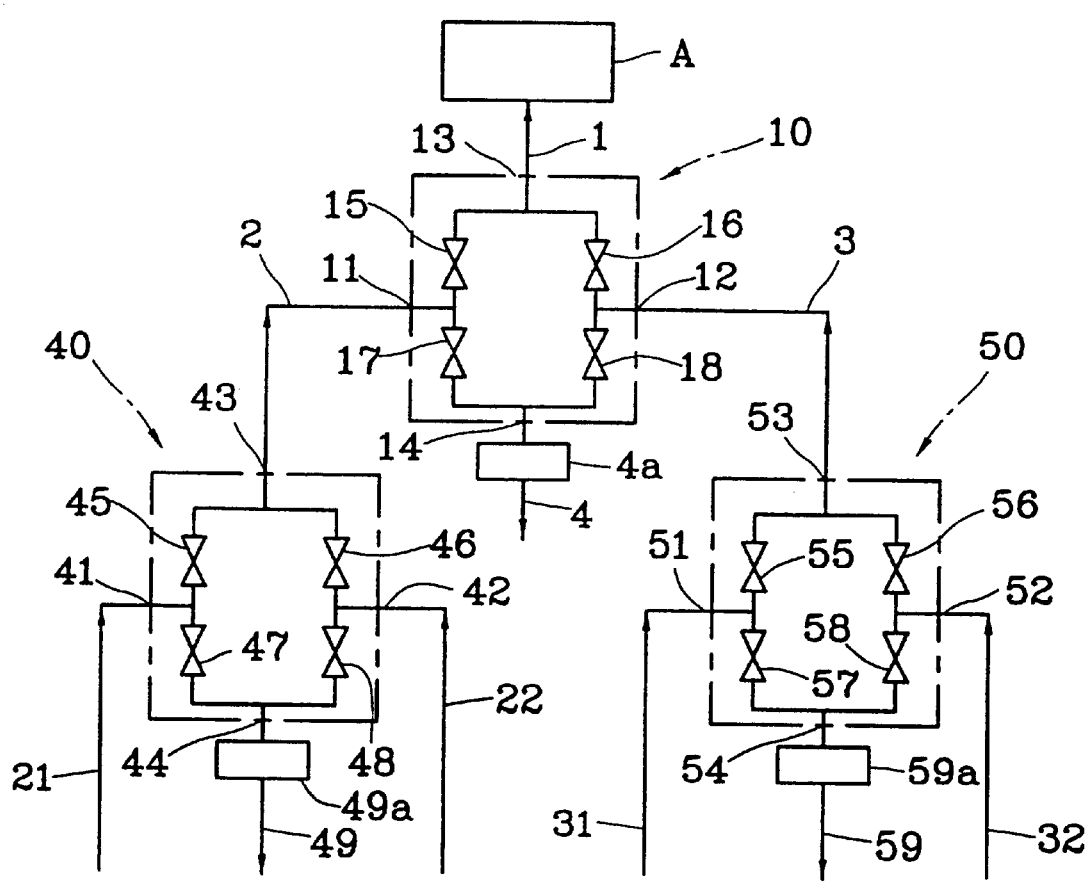
FIG. 3 is a schematic view of the third embodiment of the gas supplying apparatus according to the present invention.

FIG. 3 is a schematic view of the third embodiment of a gas supplying apparatus according to the present invention, showing an example in which a 4-way block valve is used as the switching valve instead of the above 2-connected 3-way block valve. The 4-way block valve used as switching valves 40, 50, having the same structure as the 4-way block valve of the main switching valve 10 connected to the analyzer A, respectively comprises first inflow ports 41, 51, second inflow ports 42, 52, first outflow ports 43, 53, second outflow ports 44, 54, first valves 45, 55, second valves 46, 56, and third valves 47, 57, and fourth valves 48, 58.

In the first switching valve 40, the first gas supplying passage 21, the second gas supplying passage 22, the first common gas supplying passage 2 and an exhaust passage 49 with a flow rate regulator 49a are connected to the first inflow port 41, the second inflow port 42, the first outflow port 43 and the second outflow port 44 respectively. In addition, in the second switching valve 50, the third gas supplying passage 31, the fourth gas supplying passage 32, the second common gas supplying passage 3 and an exhaust passage 59 with a flow rate regulator 59a are connected to the first inflow port 51, the second inflow port 52, the first outflow port 53 and the second outflow port 54 respectively.

In this embodiment, with respect to the first switching valve, by bringing the first valve 45 and the fourth valve 48 into the communicating state and bringing the second valve 46 and the third valve 47 into the blocking state, the gas from the first gas supplying passage 21 can flow into the first common gas supplying passage 2 and by reversing the opening and closing state, the gas from the second gas supplying passage 22 can flow into the first common gas supplying passage 2. Similarly, with respect to the second switching valve, by switching the opening and closing state of the first valve 55 and the fourth valve 58, and of the second valve 56 and the third valve 57, the gas from the third gas supplying passage 31 or the fourth gas supplying passage 32 can be switched to flow into the second common gas supplying passage 3.

Therefore, by switching the main switching valve 10 and the above two switching valves 40, 50 in a predetermined order, similar to the above, the four kinds of gases can be supplied to the analyzer A in a predetermined order, while preventing the reactive gases from mixing. In addition, the abnormality of respective valves can be easily recognized. Furthermore, since in the respective switching valves 40, 50, the exhaust passages 49, 59 each having a flow rate regulator are provided as well, the gases supplied from the respective gas supplying passages do not stagnate.

Figure 4:
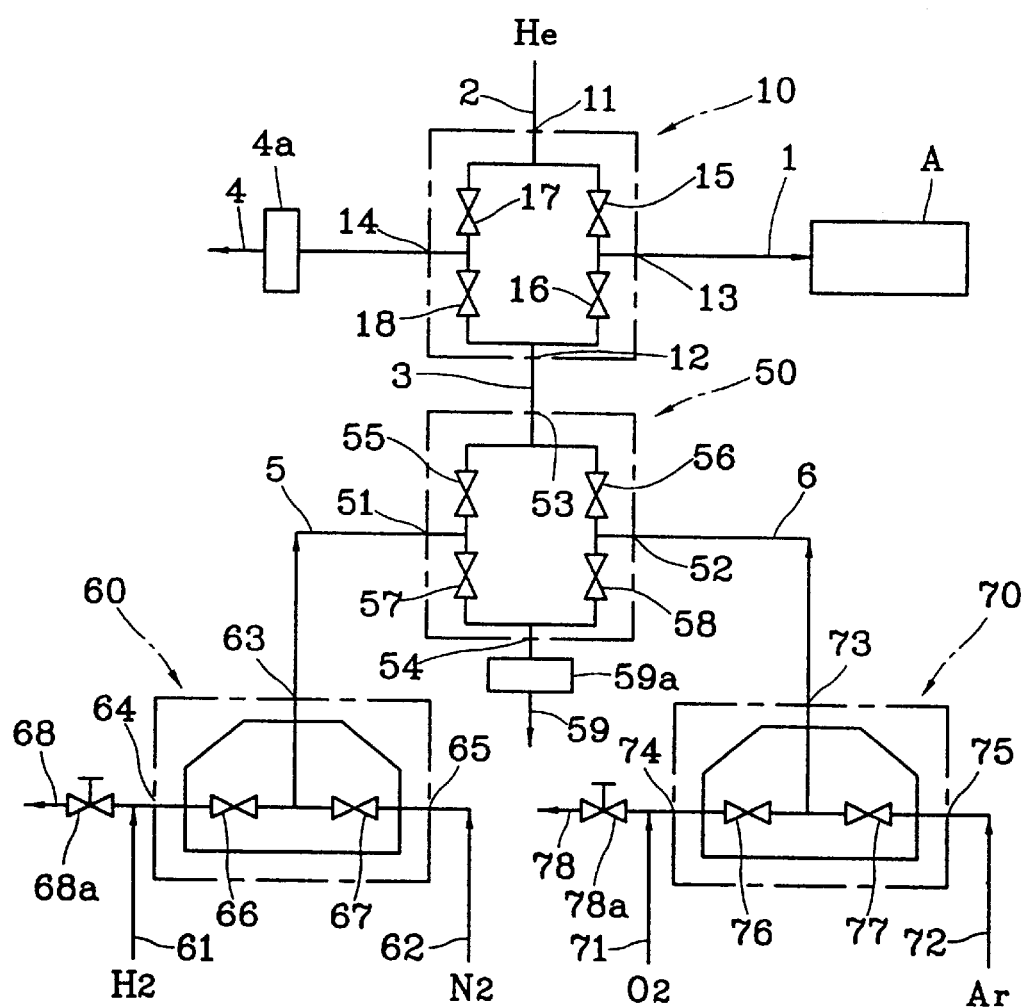
FIG. 4 is a schematic view of the fourth embodiment of the gas supplying apparatus according to the present invention.

FIG. 4 is a schematic view of the fourth embodiment of a gas supplying apparatus according to the present invention. In the apparatus, two passages of common gas supplying passages 5, 6 are respectively connected to the first inflow port 51 and the second inflow port 52 of the switching valve 50 of the above third embodiment and switching valves 60, 70 made of the 2-connected 3-way block valve are connected to the common gas supplying passages 5, 6 respectively. In addition, the first common gas supplying passage 2 connected to the first inflow port 11 of the main switching valve 10, is formed such that the gas is supplied directly without flowing through the switching valve.

The 2-connected 3-way block valve used as the switching valve 60, 70, to which two passages of gas supplying passages 61, 62 or gas supplying passages 71, 72 are switchably connected, similarly as in the second embodiment, is provided with outflow ports 63, 73 respectively connected to the common gas supplying passages 5, 6, first inflow ports 64, 74 to which the first gas supplying passage 61 or the third gas supplying passage 71 is connected, second inflow ports 65, 75 to which the second gas supplying passage 62 or the fourth gas supplying passage 72 is connected, and first valves 66, 76 and the second valves 67, 77 for switching the gas flow passage. In addition, similarly as in the above, in the first gas supplying passage 61 and the third gas supplying passage 71, exhaust passages 68, 78 with flow rate regulators 68a, 78a are branch-connected respectively.

In the case that analyzing impurities of five kinds of gases including reactive gases, such as, for example, hydrogen, oxygen, nitrogen, argon and helium, is performed by the gas supplying apparatus, hydrogen which is an reactive gas, is connected to the first gas supplying passage 61 of the switching valve 60, and oxygen is connected to the third gas supplying passage 71 of the switching valve 70, and nitrogen and argon which are non-reactive gases, are connected to the second gas supplying passage 62 and the fourth gas supplying passage 72 respectively, and helium is directly connected to first common gas supplying passage 2 connected to the 4-way block valve 10. The order of switching the gas is set to be the order of nitrogen→hydrogen→argon→oxygen→helium, thereby not analyzing the reactive gas in succession.

When analyzing nitrogen, the second valve 67, 77 of the switching valves 60, 70, the first valve 55 and the fourth valve 58 of the switching valve 50, the second valve 16 and the third valve 17 of the main switching valve 10 are brought into the communicating state, and the other valves are brought into the blocking state. Thus, nitrogen is supplied to the analyzer A, and helium, argon, hydrogen and oxygen are exhausted from the exhaust passage 4, the exhaust passage 59, the exhaust passage 68 and the exhaust passage 78 respectively.

The gas switching from nitrogen to hydrogen is performed by reversing the opening and closing state of the switching valve 60 such that the first valve 66 is brought into the communicating state and the second valve 67 is brought into the blocking state.

The gas switching from hydrogen to argon is performed by reversing the opening and closing state of the switching valve 50 such that the second valve 56 and the third valve 57 are brought into the communicating state and the first valve 55 and the fourth valve 58 are brought into the blocking state. In this case, by reversing the opening and closing state of the switching valve 60 again such that the second valve 67 is brought into the communicating state and nitrogen is exhausted from the exhaust passage 59, the stagnation time of nitrogen can be minimized and hydrogen in the common gas supplying passage 5 can be purged as well. In addition, as aforementioned, it is also possible to switch the switching valve 60 to nitrogen supply and sufficiently purge hydrogen in the passage over the analyzer A in the beginning, and then to reverse the opening and closing state of the switching valve 50.

The gas switching from argon to oxygen is performed by reversing the opening and closing state of the switching valve 70 such that the first valve 76 is brought into the communicating state and the second valve 77 is brought into the blocking state. In this case, though oxygen flows in the switching valve 50, by flowing nitrogen into the common gas supplying passage 5 and purging hydrogen during analyzing argon, even if the switching valve 50 malfunctions, hydrogen and oxygen do not mix.

The gas switching from oxygen to helium is performed by reversing the opening and closing state of the main switching valve 10, such that the first valve 15 and the fourth valve 18 are brought into the communicating state and the second valve 16 and the third valve 17 are brought into the blocking state. In this case, by reversing the opening and closing state of the switching valve 50 such that the first valve 55 and the fourth valve 58 are brought into the communicating state, and then exhausting nitrogen to be subsequently analyzed from the exhaust passage 4 of the main switching valve 10, the following gas switching can be rapidly performed. Furthermore, by reversing the opening and closing state of the switching valve 70 such that the first valve 76 is brought into the blocking state and the second valve 77 is brought into the communicating state, the oxygen in the common gas supplying passage 6 can be purged.

The gas switching from helium to nitrogen is performed by reversing the opening and closing state of the main switching valve 10, such that the second valve 16 and the third valve 17 are brought into the communicating state.

By switching the gases as above, oxygen and hydrogen do not encounter in the vicinity of the switching valve 50, and thus the safety is ensured, and there is enough time for purging nitrogen or argon which stagnate in the pipings of the gas supplying passages 62, 72, from the exhaust passage 59 during the period until the next analysis, and thus high-accuracy analysis of the impurity concentration can be safely and rapidly performed.

In addition, since even in the case that the main switching valve 10 or one of the switching valves 50, 60, 70, malfunctions, hydrogen and oxygen which are reactive gases, are not mixed, but associated with non-reactive gas to be supplied to the analyzer A without fail, the abnormality of the switching valve can be easily recognized from the measured valve of the analyzer A, as in the above case.

Figure 5:
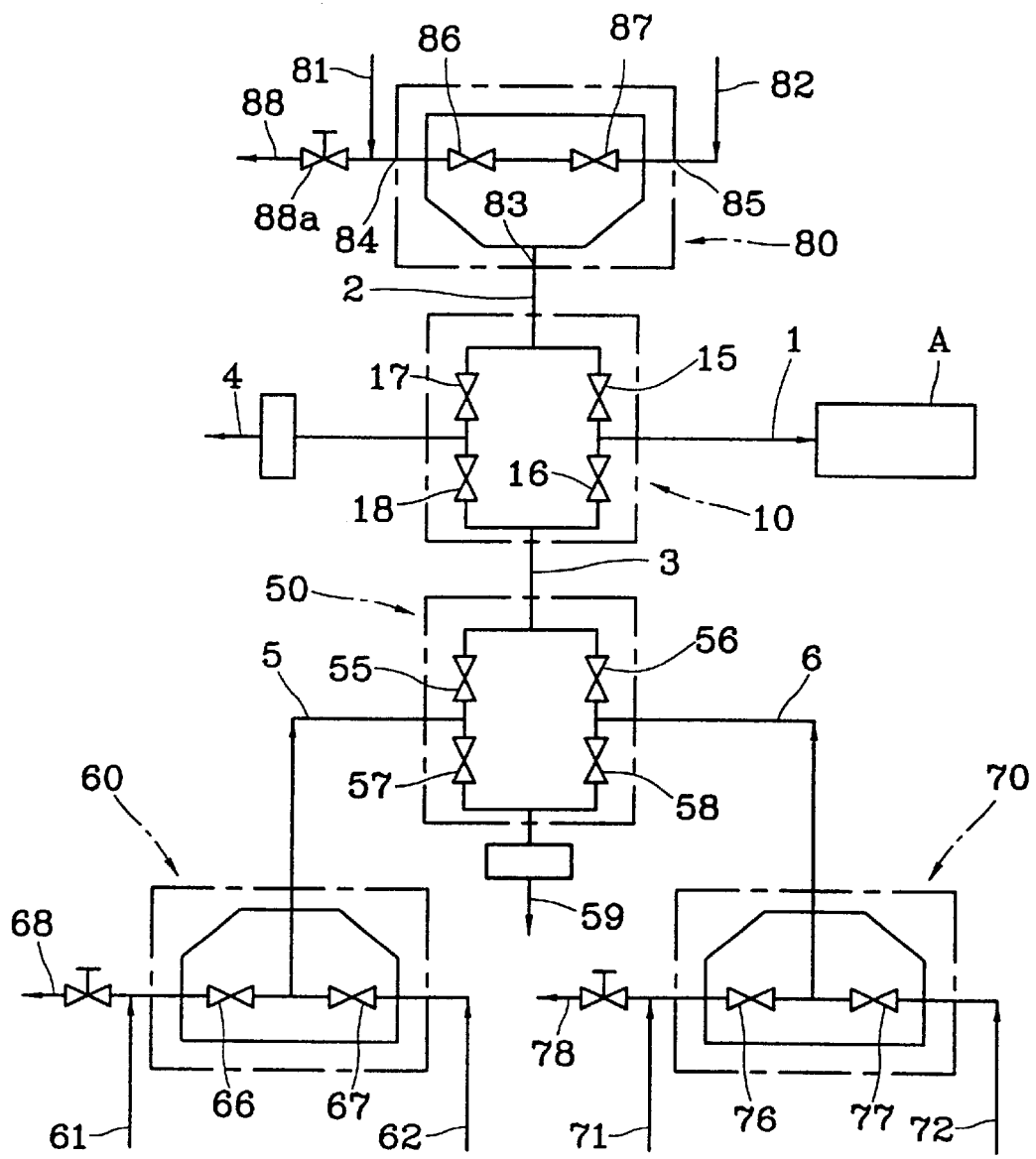
FIG. 5 is a schematic view of the fifth embodiment of the gas supplying apparatus according to the present invention.

FIG. 5 is a schematic view of the fifth embodiment of a gas supplying apparatus according to the present invention, wherein a switching valve 80 made of 2-connected 3-way block valve is connected to the first common gas supplying passage 2 according to the fourth embodiment as well. The 2-connected 3-way block valve as the switching valve 80, to which two passages of gas supplying passages 81, 82 are switchably connected as in the above case, comprises an outflow port 83 connected the first common gas supplying passage 2, first inflow port 84 connected to the fifth gas supplying passage 81, second inflow port 85 to which the sixth gas supplying passage 82 is connected, and first valve 86 and second valve 87 for switching the gas flow passage. In addition, similarly to the above case, an exhaust passage 88 with a flow rate regulator 88a is branch-connected into the fifth gas supplying passage 81.

In addition, as the main switching valve 10 and the three switching valves 50, 60, 70 are the same with those in the fourth embodiment of FIG.4, the reference numerals are attached only to the main parts and detailed explanation is omitted.

The gas supplying apparatus formed as above described, can connect maximum six kinds of gases and switchably supply them in the six passages of the first~the sixth gas supplying passages 61, 62, 71, 72, 81, 82, and up to three kinds of reactive gases can be applied as well. Furthermore, in the first common gas supplying passage 2, by connecting a plurality of switching valves such as the switching valves 50, 60, 70, various kinds of gases can be switchably supplied.

As described in the above, according to the present invention, as the switching of the gases to be supplied to the instrument can be rapidly performed and mixing between reactive gases can be avoided, for example, high-accuracy analysis of the trace impurities for a plurality of the sample gases can be safely and rapidly performed.

What is claimed is:

1. A process for supplying gas from a gas supplying apparatus to an analyzing instrument, said apparatus including a main switching valve in the form of a 4-way block valve having two inflow ports and two outflow ports, a connection passage connected to the analyzing instrument to which a first of the two outflow ports is connected, an exhaust passage having a flow rate regulator to which a second of the two outflow ports is connected, a pair of common gas supplying passages respectively connected to the two inflow ports of the 4-way block valve, one of first or second switching valves connected to each of the pair of common gas supplying passages respectively, first and second gas supplying passages connected to the first switching valve, and third and fourth gas supplying passages connected to the second switching valve, said process comprising:

connecting said first switching valve at said first gas supplying passage to a first source of a first reactive gas and at said second gas supplying passage to a second source of a first non-reactive gas, and connecting said second switching valve at said third gas supplying passage to a third source of a second reactive gas and at said fourth gas supplying passage to a fourth source of a second non-reactive gas;

supplying the second non-reactive gas from the second switching valve to the main switching valve, in the case of supplying the first reactive gas to the instrument from the first switching valve via the main switching valve;

switching the first switching valve supplying the first reactive gas in order to supply the first non-reactive gas, in the case of switching the first reactive gas to be supplied to the instrument to the second reactive gas coming from the second switching valve; and switching the main switching valve such that the first reactive gas to be supplied to the instrument is switched to the second reactive gas coming from the second switching valve after the concentration of the first reactive gas from the first switching valve is lowered below a predetermined concentration.

* * * * *